United States Patent
Shah et al.

(10) Patent No.: US 7,162,289 B2
(45) Date of Patent: Jan. 9, 2007

(54) METHOD AND APPARATUS FOR ENHANCING THE INTEGRITY OF AN IMPLANTABLE SENSOR DEVICE

(75) Inventors: Rajiv Shah, Rancho Palos Verdes, CA (US); Yanan Zhang, Valencia, CA (US); Rebecca Gottlieb, Culver City, CA (US); Bahar Reghabi, Marina Del Rey, CA (US); Michael Miller, Los Angeles, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 339 days.

(21) Appl. No.: 10/335,574

(22) Filed: Dec. 31, 2002

(65) Prior Publication Data

US 2004/0064156 A1 Apr. 1, 2004

Related U.S. Application Data

(60) Provisional application No. 60/414,142, filed on Sep. 27, 2002.

(51) Int. Cl.
*A61B 5/00* (2006.01)
*A61B 5/05* (2006.01)
*C12M 1/00* (2006.01)
*C12Q 1/00* (2006.01)

(52) U.S. Cl. ............... 600/345; 600/309; 600/365; 204/403.01; 204/403.14

(58) Field of Classification Search ............... 204/403.01–403.06, 403.11–403.14, 400, 204/403.1; 600/486, 488, 561, 300, 316, 600/322–325, 372, 373, 459, 462, 466, 467
See application file for complete search history.

(56) References Cited

U.S. PATENT DOCUMENTS

| 4,191,193 | A | * | 3/1980 | Seo ........................ 600/488 |
| 4,730,389 | A | | 3/1988 | Baudino et al. |
| 4,765,860 | A | * | 8/1988 | Ueno et al. ............ 156/272.6 |
| 5,019,096 | A | | 5/1991 | Fox, Jr. et al. |
| 5,039,491 | A | | 8/1991 | Saaski et al. |
| 5,085,223 | A | * | 2/1992 | Lars et al. ............. 600/488 |
| 5,272,012 | A | * | 12/1993 | Opolski ................ 428/423.1 |
| 5,596,988 | A | * | 1/1997 | Markle et al. ........... 600/353 |

(Continued)

OTHER PUBLICATIONS

PCT International Search Report as issued in International Application No. PCT/US03/28854, Mailing date Aug. 9, 2004.

*Primary Examiner*—Charles A Marmor, II
*Assistant Examiner*—Patricia Mallari
(74) *Attorney, Agent, or Firm*—Foley & Lardner LLP

(57) ABSTRACT

A method and apparatus for enhancing the integrity of an implantable sensor. Voids formed between an outer tubing and a sensor substrate or spacing element may be back-filled with a curable, implantable material, minimizing the extent to which unwanted fluids diffuse within the sensor. An enzyme or protein matrix pellet below the sensor window may be pre-treated with a reducing agent to enhance its bond stability, and to reduce undesired swelling that may cause the sensor window to detach or leak. The bonding between the enzyme pellet and a hydrogel layer may be reinforced by application of an intervening bonding layer of a protein material, such as human serum albumin (HSA). The size of the window may be minimized by minimizing the size of an underlying electrode, providing reduced flux and lengthening sensor. A coating may be deposited on the surface of the sensor leads, providing stiffening and lubrication.

30 Claims, 13 Drawing Sheets

U.S. PATENT DOCUMENTS

| | | | |
|---|---|---|---|
| 5,696,314 A * | 12/1997 | McCaffrey et al. | 205/778 |
| 5,957,970 A | 9/1999 | Shobert et al. | |
| 5,972,199 A * | 10/1999 | Heller et al. | 205/777.5 |
| 5,980,478 A * | 11/1999 | Gorsuch et al. | 604/5.04 |
| 6,019,729 A * | 2/2000 | Itoigawa et al. | 600/488 |
| 6,024,693 A * | 2/2000 | Schock et al. | 600/18 |
| 6,081,736 A * | 6/2000 | Colvin et al. | 600/377 |
| 6,117,086 A * | 9/2000 | Shulze | 600/488 |
| 6,484,045 B1 | 11/2002 | Holker et al. | |
| 2003/0050547 A1* | 3/2003 | Lebel et al. | 600/364 |

* cited by examiner

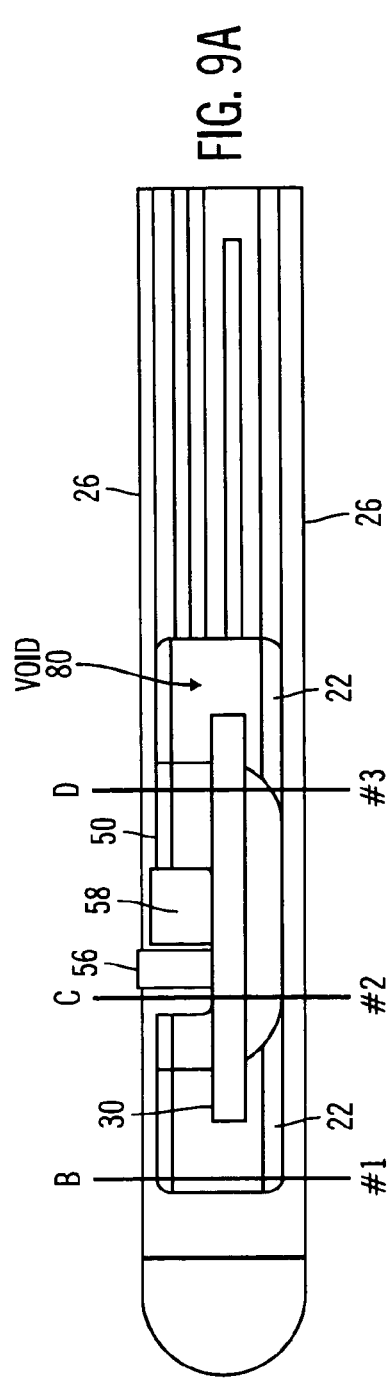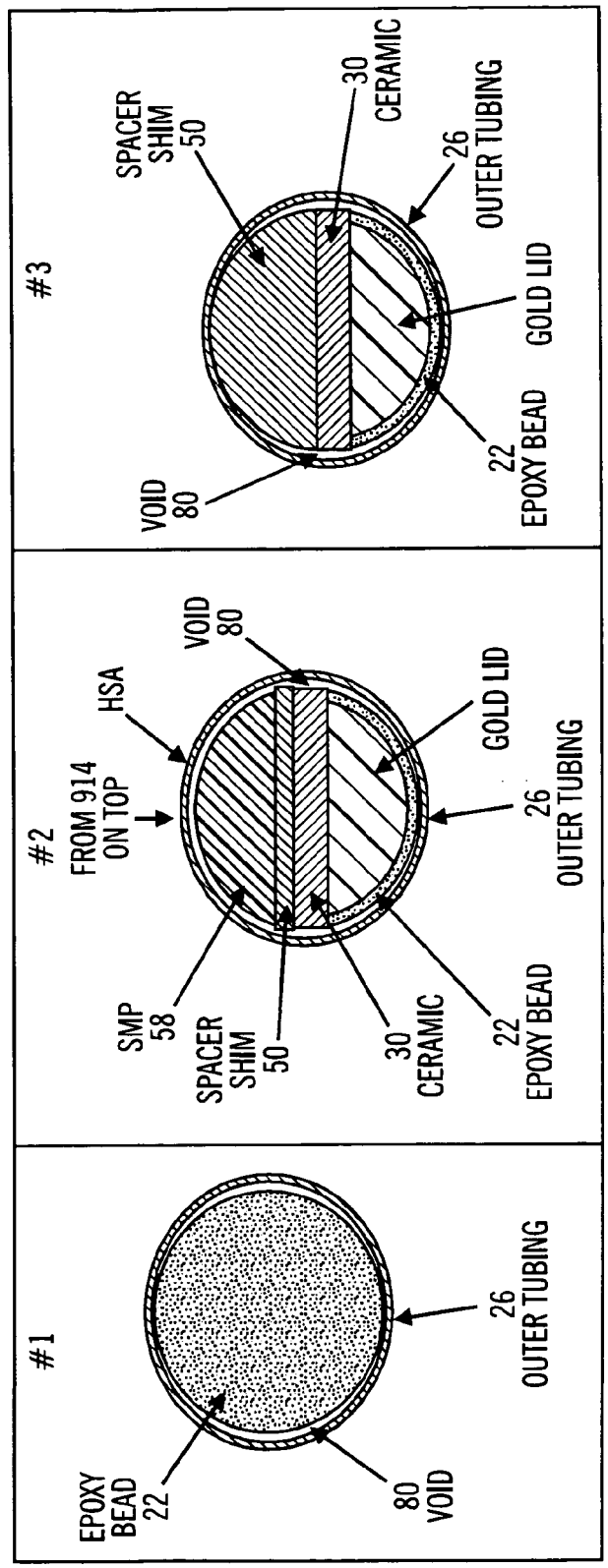

METHOD AND APPARATUS FOR ENHANCING THE INTEGRITY OF AN IMPLANTABLE SENSOR DEVICE

CROSS-REFERENCE TO RELATED APPLICATIONS

Embodiments of the present invention relate to U.S. Provisional Application Ser. No. 60/414,142, filed Sep. 27, 2002, entitled "Method and Apparatus for Enhancing the Integrity of an Implantable Sensor Device," which is incorporated by reference herein and is a basis for a claim of priority.

BACKGROUND

1. Field of the Invention

The present invention relates generally to the field of medical devices, and, more specifically, to sensor structures for medical implants.

2. Related Art

The combination of biosensors and microelectronics has resulted in the availability of portable diagnostic medical equipment that has improved the quality of life for countless people. Many people suffering from disease or disability who, in the past, were forced to make routine visits to a hospital or doctor's office for diagnostic testing currently perform diagnostic testing on themselves in the comfort of their own homes using equipment with accuracy to rival laboratory equipment.

Nonetheless, challenges in the biosensing field have remained. For example, although many diabetics currently utilize diagnostic medical equipment in the comfort of their own homes, the vast majority of such devices still require diabetics to draw their own blood and inject their own insulin. Drawing blood typically requires pricking a finger. For someone who is diagnosed with diabetes at an early age, the number of self-induced finger pricks over the course of a lifetime could easily reach into the tens of thousands. In addition, the number of insulin injections may also reach into tens of thousands.

Some medical conditions have been amenable to automated, implantable sensing. For example, thousands of people with heart conditions have had pacemakers or defibrillators implanted into their bodies that utilize sensors for monitoring the oxygen content of their blood. Ideally, these sensors should be able to determine whether, for example, a person's heart is running very efficiently at a high heart rate or whether a person's heart has entered fibrillation. In order to effectively make this determination, an accurate sensor must be employed. Unfortunately, oxygen sensors implanted into the body have, thus far, typically required frequent and periodic recalibration and replacement.

An important aspect of implantable sensors, regardless of the application, is the integrity of the sensor structure itself. When the integrity of the sensor structure fails, either partially or completely, undesired fluids and cells may diffuse into the sensor structure, causing unstable sensing performance or sensor failure. For example, once the integrity of an implanted sensor has become compromised, blood may pool and clot around electrodes, fibrous growths may develop over the top of electrodes, and softer elements (e.g., enzymes, protein matrices, membranes and the like) of the sensor may deteriorate or be digested.

Once a sensor structure has been compromised in this manner, the sensor must be replaced, requiring an explantation procedure for the old sensor and an implantation procedure for a new sensor. These surgical procedures are semi-invasive, expensive and inconvenient. Further, unless the sensor fails completely, it may be difficult to detect the exact status of the sensor without explanting it first.

In clinical experiments, complications have arisen during implantation of a sensor due to the flexibility of the sensor structure. A surgeon may find that the sensor lead buckles under the axial pressure exerted by the surgeon to force the sensor through the introducer, particularly if a kink is formed in the introducer. As an example, the introducer 140 shown in FIG. 11 has a 45 degree kink 142 formed therein. As an insufficiently stiff and/or lubricious sensor is advanced through the introducer 140, the kink 142 may obstruct the sensor and cause it to buckle in the lateral direction (shown by arrow 144) rather than moving forward in the axial direction of the introducer 140 (shown by arrow 146). As a result of buckling, the sensor may be damaged.

A further complication exists in that the surgeon, while placing the sensor into the introducer, may grip the sensor lead 150 away from the tip where the sensor 152 is located and towards the proximal end of the sensor lead, as shown in FIG. 12A where the gripping point is represented by a pair of crosshatched boxes 154, 156. As a result of the insufficient stiffness of the sensor lead 150, it may hang in a flaccid state when gripped in this manner, making it difficult to place into the introducer. Thus, the surgeon may instead grip the sensor lead 150 closer to the tip, as shown in FIG. 12B, in order to more easily place the sensor lead 150 into the introducer 100 (FIG. 11). However, while gripping the sensor lead 150 in this manner, the surgeon may inadvertently damage the sensor, for example, by exerting excessive pressure on the sensor or because the sensor is made from fragile materials.

Yet another complication resulting from an insufficiently stiff sensor, as shown in FIG. 13, is that when inserted in a vessel 162, the sensor 152, under pressure from fluid flowing through the vessel 162, may rest against a side-wall 166 of the vessel 162 rather than near the center of the vessel 162. This may result in a reduction in the accuracy of the sensor readings or may cause vessel irritation.

Accordingly, there is an industry need for a sensing apparatus that may be implanted into the body and that may remain in the body reliably for extended periods of time. There is a further need in the industry for a sensor structure having enhanced integrity to ensure long-term protection of the sensitive elements of the sensor structure. There is a further need in the industry for a sensor structure that is sufficiently stiff to facilitate steerability of the sensor structure into the body. There is a further need in the industry for a sensor structure that has a surface that is lubricious enough to facilitate implantation of the sensor structure into the body.

SUMMARY OF THE DISCLOSURE

Embodiments of the present invention relate generally to implant devices having a sensor structure for sensing a chemical concentration in a cavity or vessel within the body of a patient. Particular embodiments relate to tubing materials and treatments, enzyme or protein matrix treatments, window bonding materials, void back-fill materials, minimized electrode and window size, and methods for making and/or applying the same, which address one or more of the concerns and demands in the industry as noted above.

A sensor device in one embodiment includes a sensor substrate having sensor electronics and a sensor electrode, a spacer element adjacent to the electrode of the sensor substrate, an enzyme or protein matrix resting within a window region of the spacer element, an outer tubing surrounding the other elements and having a window opening above the enzyme or protein matrix, and a hydrogel layer above the enzyme or protein matrix, which seals the window opening in the outer tubing.

In accordance with one or more embodiments of the invention, the enzyme or protein matrix may be bonded to the hydrogel layer by an intervening bonding layer. The bonding layer may be made of any bio-compatible material that has the adhesive properties of a protein and that is permeable to a sensor-specific substance, such as glucose, for example, or other substance selected for measurement. According to one or more embodiments of the invention, the bonding layer may comprise a layer of protein, such as human serum albumin (HSA), collagen, fibrin or other bonding protein. In other embodiments, the bonding layer may comprise a synthetic bonding material, such as, for example, a polypeptide.

In one or more embodiments, spatial voids between the outer tubing and the internal elements of the sensor module may be back-filled to inhibit diffusion of unwanted fluids within the sensor device. In one or more embodiments, the back-fill material may be, for example, a curable, implantable material, such as, for example, silicone, epoxy, bone cement, foam or the like.

In one or more embodiments, the size of the window opening may be reduced to minimize the window perimeter that is subject to stress and wear, as well as to reduce the flux and thus extend the useful life of the enzyme or protein matrix. The size of the underlying electrode may also be reduced by controlling the processes used to form the electrode.

In one or more embodiments of the invention, the enzyme or protein matrix may be a pre-treated enzyme or protein matrix pellet, washed with a reducing agent to prevent excessive swelling. The reducing agent may be, for example, Ascorbate. As a result, the enzyme or protein matrix pellet may be less prone to destabilization and less likely to cause detachment of the overlying hydrogel layer.

Embodiments of the invention may be further directed to processes for making a sensor device as described above. In one or more embodiments, a substrate is encapsulated between two beads; one or more molded spacer elements is inserted between the beads; the beads, the substrate and the spacer elements are covered by an outer tubing; a window opening is cut into the outer tubing; an enzyme or protein matrix is inserted into the window opening; and a hydrogel layer is used to seal the window opening over the enzyme or protein matrix.

In one or more embodiments of the invention, spatial voids between the outer tubing and the sensor substrate and/or the spacer element may be back-filled prior to insertion of the enzyme or protein matrix. This back-filling process may be implemented by injecting back-fill material into the spatial voids via the open window, and subsequently curing the back-fill material. The back-fill material may be in a flowing or liquid state during injection, and in a non-flowing state after curing. In another embodiment, the back-filling process may be implemented by placing pre-molded structures into the spatial voids during final assembly.

In one or more embodiments of the invention, the enzyme or protein matrix may be treated with a reducing agent prior to its insertion into the window opening. The treatment may be, for example, a wash of the enzyme or protein matrix in a solution with a reducing agent, such as, for example, Ascorbate, cyanoborohydride, or the like.

In accordance with another embodiment of the invention, a bonding material may be applied as a bonding layer over the enzyme or protein matrix prior to application of the hydrogel layer. Application of the bonding material may be through, for example, a volumetric dispenser such as a syringe or dropper. Bonding between the bonding layer, the enzyme or protein matrix, and the hydrogel layer may be facilitated by application of a cross-linking agent, such as, for example, gluteraldehyde, ultra violet light or the like. Temperature controlled cross-linking may also be used.

These and other embodiments and advantages of the invention will be apparent to one of skill in the art from the accompanying detailed description and drawings. Embodiments of the invention can be practiced individually or in any suitable combination.

BRIEF DESCRIPTION OF THE DRAWINGS

FIG. 9A is a transparent top-down view of a sensing apparatus showing void spaces for back-filling in accordance with one or more embodiments of the invention.

FIGS. 9B, 9C and 9D are axial, cross-sectional views of a sensing apparatus showing void spaces for back-filling in accordance with one or more embodiments of the invention.

DETAILED DESCRIPTION OF PREFERRED EMBODIMENTS

Figure 1:
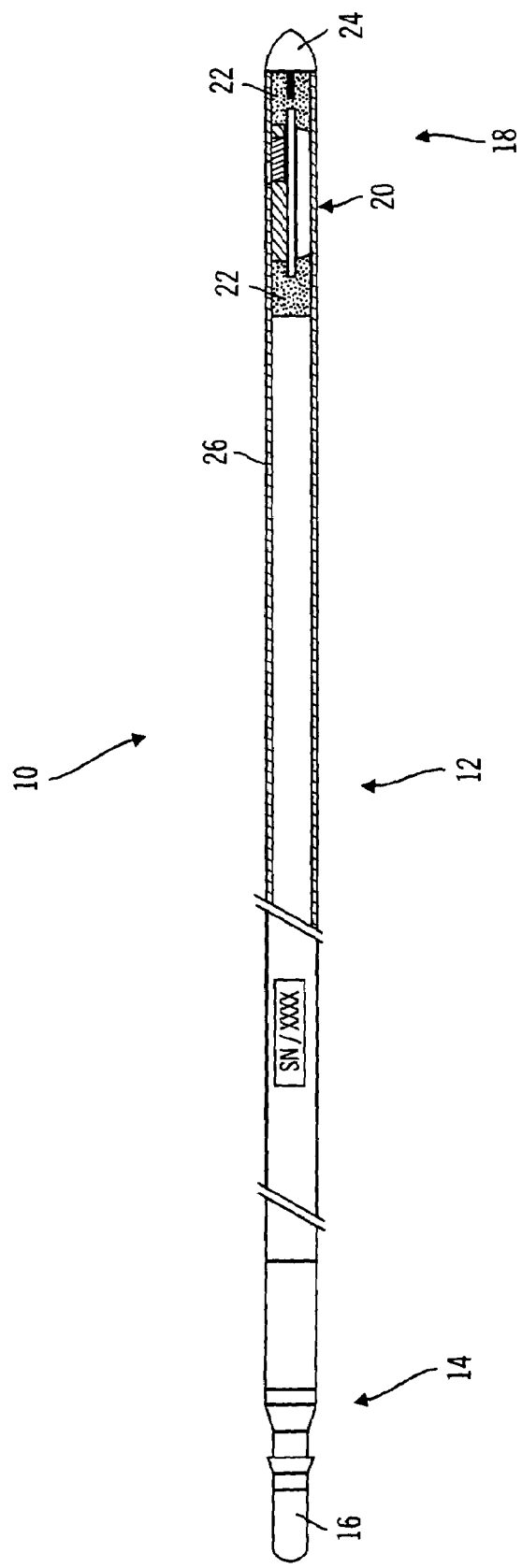
FIG. 1 is a perspective view, with partial cut-away, of a generalized sensing apparatus configuration in accordance with one or more embodiments of the invention.

The present invention relates generally to sensor structures for electronic medical implant devices, and to methods for making such sensors. This description is not to be taken in a limiting sense, but is made merely for the purpose of illustrating the general principles of example embodiments of the invention. The scope of the invention is best defined by the appended claims. In the following description, numerous specific details are set forth to provide a more thorough description of one or more embodiments of the invention. It will be apparent, however, to one skilled in the art, that the invention may be practiced without these specific details. Other embodiments may be utilized and structural changes may be made without departing from the scope of the present invention. Though described herein as a sensor for monitoring physiological parameters such as glucose level, for example, it will be apparent that embodiments of the invention are also applicable to other sensor applications including, but not limited to oxygen, ion, neurotransmitter, nitric oxide, pH, lactate, temperature or pressure sensing and the like.

Embodiments of the present invention comprise a sensing apparatus including, without limitation, a sensor module, a sensor lead and a connector. As will be explained below in greater detail, the sensor module may comprise, without limitation, an enzyme or protein matrix, one or more spacers and sensor electronics. The lead may comprise, without limitation, a core, a conductor, a first tubing and a second, or outer tubing. When implanted, the enzyme or protein matrix in the sensor module reacts with chemicals that are present in the implant environment and that pass through a window or porous material, such as, for example, glucose permeable membranes, silicones polyurethanes or the like, in the sensor module. As a result, the sensor electronics produce an electrical signal representative of a chemical condition in the implant environment. The electrical signal is applied to the conductor portion of the lead and conducted to other suitable signal processing means for use in a given medical application. Applications may include, but are not limited to, monitoring of internal conditions in a patient, feedback control of chemical disbursements or stimulus to a patient, and other biochemical sensing and control applications or monitoring systems, such as, for example, therapy monitoring, ex vivo systems, external sustaining fluid circuits, ECMO, dialysis, bypass, heart and lung machines, neurological applications, drug delivery systems, predictive monitoring of diseases states, non-disease monitoring of body processes, and the like.

In embodiments of the sensing apparatus, each element of the sensing apparatus may be modified separately or in conjunction with another element according to the application or environment in which the sensing apparatus is used. Thus, the sensing apparatus may be seen as a plurality of individual elements, each of which may be modified and combined with one another to provide a sensing apparatus that may be used in a variety of applications, in a variety of environments, and implanted in a variety of locations.

Further description of sensor substrates, sensor leads and general sensing apparatus structures that may be employed in conjunction with embodiments of the present invention are provided in the following U.S. patent applications, the contents of which are incorporated herein by reference: U.S. application Ser. No. 10/033,720, filed Dec. 27, 2001, entitled "Electronic Lead for a Medical Implant Device, Method of Making Same, and Method and Apparatus of Inserting Same;" U.S. application Ser. No. 10/036,093, filed Dec. 28, 2001, entitled "Sensing Apparatus and Process;" U.S. application Ser. No. 10/038,276, filed Dec. 31, 2001, entitled "Sensor Substrate and Method of Fabricating Same;" and U.S. application Ser. No. 10/034,338, filed Dec. 28, 2001, entitled "Implantable Sensor Electrodes and Electronic Circuitry."

As described previously, it is advantageous in the biosensing field to have an implantable sensing device that is sufficiently robust in its design and manufacture for long term use. However, over time, the integrity of an implanted sensing device may be compromised in such a manner that blood and other fluids are able to diffuse within the body of the sensor module, resulting in unstable performance or failure of the device. The following description discusses several methods and structure for addressing the sensor integrity issue, including a method and structure for minimizing the free volume within the sensor into which the undesired fluids can diffuse, as well as methods and structure for enhancing the integrity of the window region of the sensor, e.g., by washing an enzyme or protein matrix pellet with a reducing agent, by bonding a hydrogel layer to the enzyme or protein matrix pellet with an intervening bonding layer of protein, and by reducing the size of the sensor window. Also discussed are methods and structure to improve the stiffness and lubricity of a sensor lead. Each of these methods and structure is described below in the context of one or more embodiments of a sensor device and one or more embodiments for making and using a sensor device.

FIG. 1 shows a generalized sensing apparatus configuration according to an embodiment of the present invention. A sensing apparatus 10 includes a sensor lead 12, a first end 14 comprising an electrical connector 16 and a second end 18 comprising a sensor module 20. Beads 22 are molded, or otherwise coupled to or formed onto each end of an electrical substrate disposed in the sensor module 20. An ogive, or bullet-shaped, tip 24 attaches to a bead 22 that is opposite the sensor lead 12 such that the entire assembly is streamlined in a fluidic environment, such as a bloodstream. The assembly is also streamlined for ease of implanting, whether or not such implanting is performed in a fluidic area of the body, such as, for example, the peritoneum, subcutaneous tissue, the spine, brain, muscle tissue and the like. The sensor lead 12 comprises outer tubing 26 that attaches to the ogive tip 24. The entire sensing apparatus 10 may be placed in a vein or other suitable areas within a human body, including, but not limited to the abdominal cavity, the peritoneum, subcutaneous tissue, the spine, brain, and the like. Such an apparatus may also be used in animals or in vitro applications.

The connector 16 may be a male, female or other type of connector. The connector 16 may provide for multiple conductive paths, thereby accommodating a variety of sensor lead 12 configurations. Also, the connector 16 may be made from a variety of materials. For example, the connector 16 may be made from any material that is electrically conductive yet chemically inert. The connector 16 may also be constructed in one or more embodiments to conduct other forms of signals, including, but not limited to optical signals carried by optical leads.

Figure 2B:
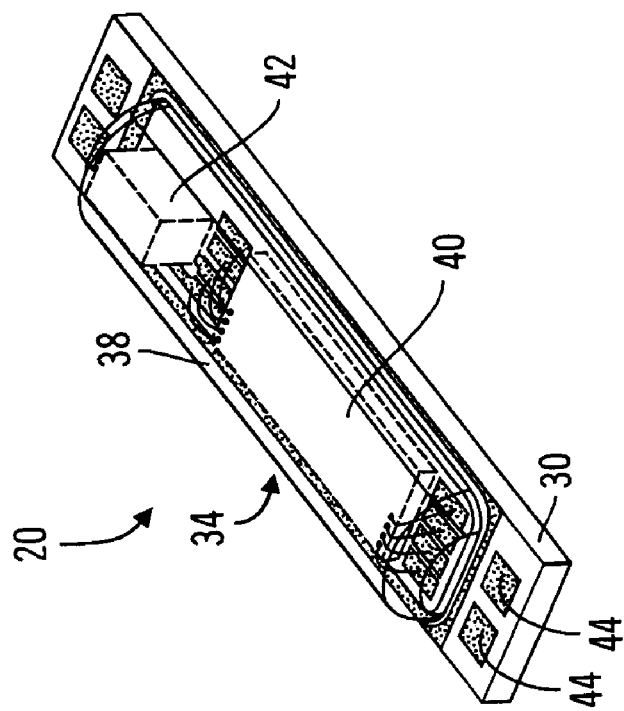
FIG. 2B is a perspective view of an electronics side of a generalized sensor module configuration in accordance with one or more embodiments of the invention.
Figure 2A:
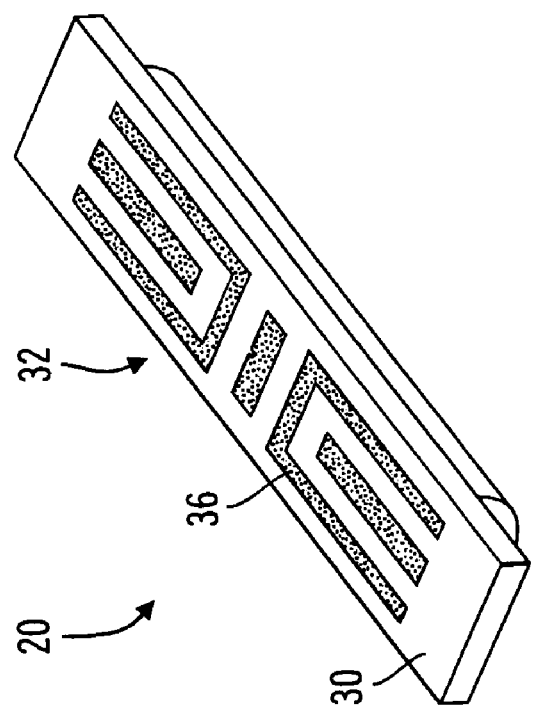
FIG. 2A is a perspective view of an electrode side of a generalized sensor module configuration in accordance with one or more embodiments of the invention.

FIGS. 2A and 2B show a generalized sensor configuration according to an embodiment of the present invention. A sensor module 20 may include a substrate 30 having a sensing element side 32 and an electronics side 34. The substrate 30 may be made from ceramic or other suitable materials including, but not limited to silicon, gallium arsenide or the like. As can be seen in FIG. 2A, electrodes 36 may be formed onto the sensing element side 32 of the substrate 30, for example, by deposition, plating or other suitable process common in the art. The electrodes 36 may interface with a sensing element (not shown) which will be described below.

As can be seen in FIG. 2B, the electronics side 34 of the substrate 30 may include a lid 38 that covers a variety of electronics, such as, for example, an integrated circuit 40 and a power capacitor 42. The electronics side 34 of the substrate 30 may also include welding pads 44 to which wire leads may be welded as well as other types of pads and traces common to electronic circuitry. The electrodes 36 and the electronics on the electronics side 34 of the substrate 30 operate with further sensor structure to provide electrochemical measurement, for example, consistent with the operation of the sensor described in U.S. application Ser. No. 10/036,093, filed Dec. 28, 2001, entitled, "Sensing Apparatus and Process," the description of which is incorporated herein by reference. According to one embodiment of the invention, the sensor module 20 may be utilized for oxygen sensing. However, the sensor module is not limited to this application and, thus, may be utilized in other applications including, but not limited to ion, neurotransmitter or nitric oxide sensing. As another example, the sensor module may be used in connection with protein matrices or antibody matrices for applications involving enzymatic reactions, florescence reactions, optical changes, piezochemical reactions, piezoelectric reactions, and the like to detect substance levels in the blood or other bodily fluids.

Figure 3A:
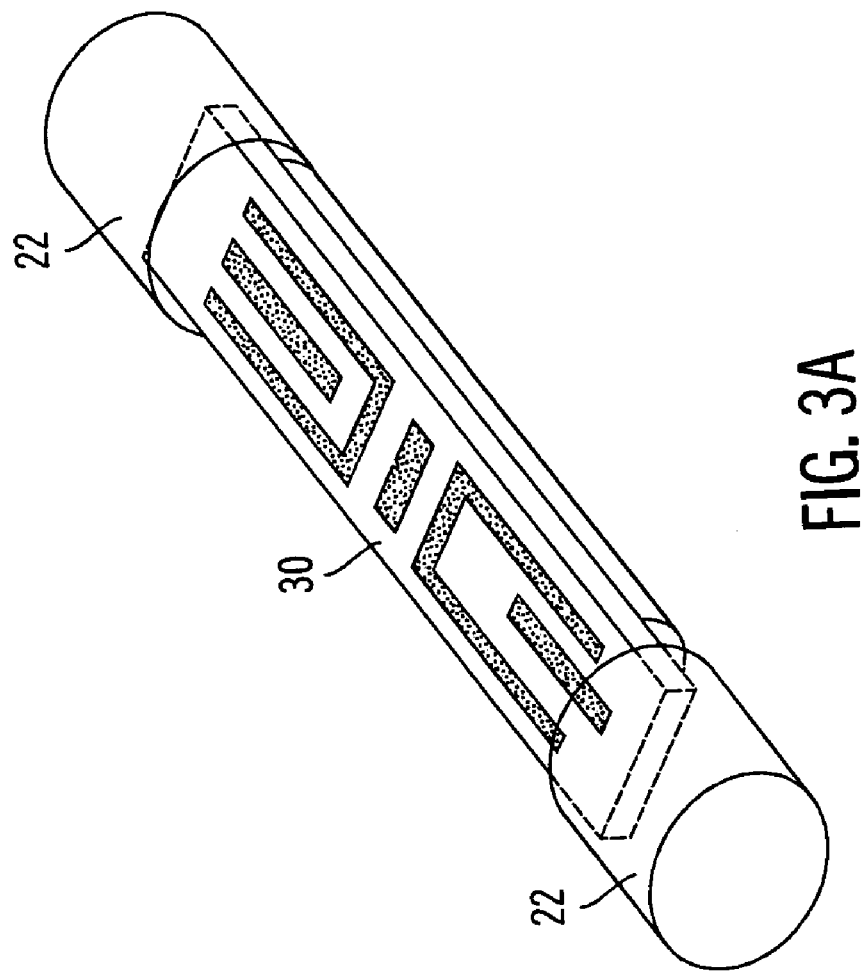
FIG. 3A is a perspective view of an electrode side of a generalized sensor module configuration with encapsulated ends in accordance with one or more embodiments of the invention.

FIG. 3A shows further details of a generalized sensor configuration according to an embodiment of the present invention. In FIG. 3A, a portion of the electrode pattern may be encapsulated by the beads 22.

Beads 22 may be molded over the ends of the substrate 30 such that welding pads and any wires welded to the welding pads are encapsulated within the beads 22. The beads 22 may be formed over the ends of the substrate 30 using a mold. The substrate 30 may be placed into the mold and the ends of the substrate 30 subsequently covered with an epoxy or other encapsulating material. In other embodiments, the beads 22 may be formed and coupled to the substrate 30 by other suitable means including, but not limited to compression fit or other mechanical fit. Examples of material that may be used to form the beads 22 include, but are not limited to, epoxy, plastic, silicone, stainless steel, metal, foam rubber or the like, or a combination of these or other suitable materials.

In one or more embodiments, the beads 22 may be formed to encapsulate the electronics side of the substrate (opposite the electrodes) to provide greater protection and support of the substrate. The beads 22 may also encapsulate a core of the sensor lead 12, thereby giving the core an anchor.

Figure 4:
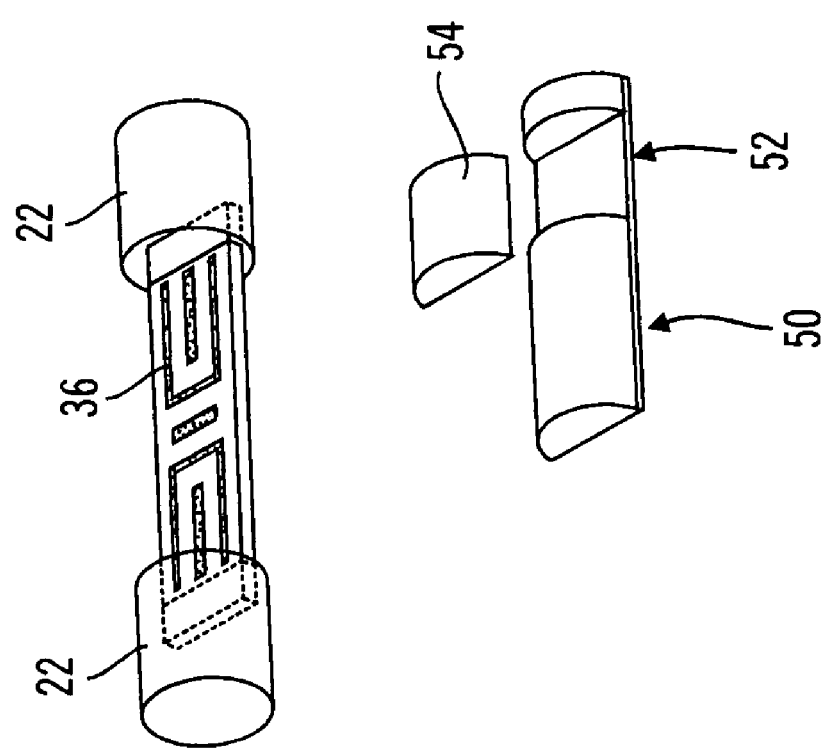
FIG. 4 is a partially-exploded, perspective view of a sensor module with spacers in accordance with one or more embodiments of the invention.

FIG. 4 shows a sensor module with spacing elements in partially exploded view. The first spacing element 50 may be placed over the electrodes 36, fitting into a recess between the beads 22. The first spacing element 50 may be thought of as a spacer shim because it has the function of maintaining a certain distance or space between the electrodes 36 and an enzyme or protein matrix which will eventually be placed within the sensor module 20. However, the first spacing element 50 provides not only mechanical support but provides performance characteristics as well. For example, the first spacing element 50 may be made from a foam or other porous membrane. The actual material used for the first spacing element 50 may depend on the application. For applications requiring that oxygen pass through the first spacing element 50, silicone may be used as the first spacing element 50 material. In addition, the shape of the first spacing element 50 may vary depending on the geometry of the sensor and other geometries of the module as well as desired characteristic of the device. For example, reducing the height of the first spacing element 50 may provide faster sensor response times.

The floor 52 of the first spacing element 50 may be such that it allows the passage of oxygen. If, for example, the first spacing element is made from silicone, polydimethylsiloxane or a porous polymer, the floor 52 of the first spacing element 50 will pass oxygen but will not pass other compounds found in the bloodstream, such as glucose.

Figure 5:
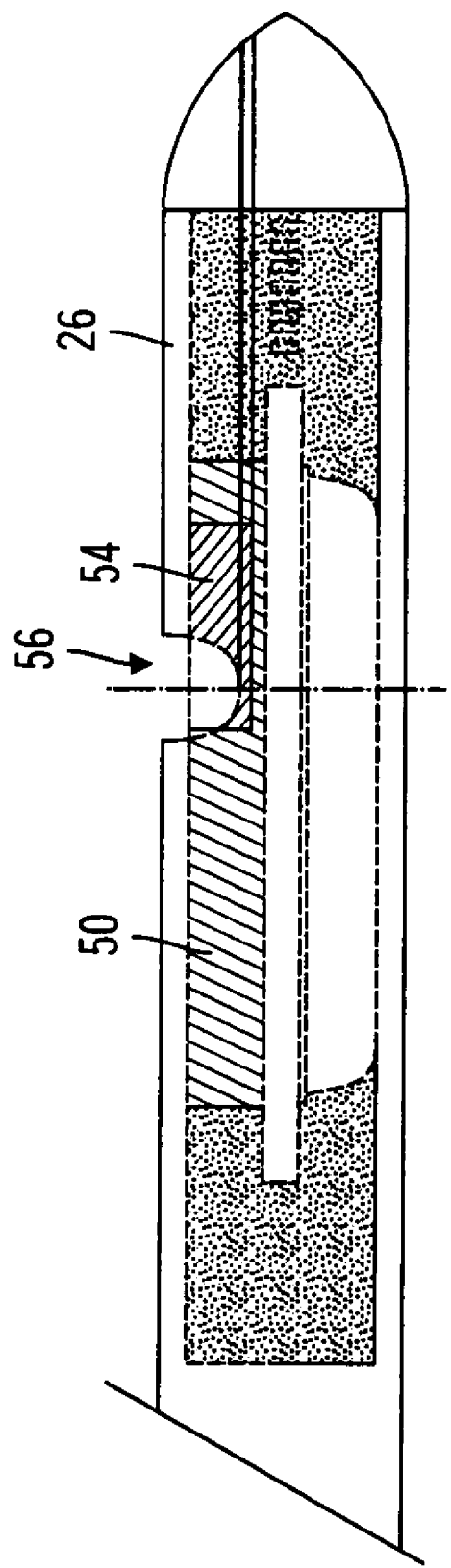
FIG. 5 is a cross-sectional side view showing a window formed in an outer tubing of a sensing apparatus in accordance with one or more embodiments of the invention.

The second spacing element 54 fits within a recess or receptacle in the first spacing element 50 and provides support for a window that may be cut or otherwise formed in the outer tubing 26 that covers the sensor module 20. FIG. 5 provides a side view showing a window 56 cut into the outer tubing 26, adjacent to the location of second spacing element 54. After the window 56 has been cut, as will be explained below, the second spacing element 54 may be removed from the recess or receptacle in the first spacing element and discarded. An enzyme, protein matrix or other sensing catalyst may be disposed in or inserted into the recess or receptacle of the first spacing element 50 in place of the removed second spacing element 54. The spacing elements 50, 54 may be made from silicone or polydimethylsiloxane, or a porous polymer, for example, or other suitable material.

The enzyme or protein matrix and spacer may be used to fine tune sensor performance. The size and configuration of the enzyme or protein matrix and spacer may be modified to effect a variety of sensing characteristics. For example, the enzyme or protein matrix and spacer size and configuration may be modified to improve dynamic range, reduce noise due to oxygen transients, and increase sensing apparatus lifetime. The configuration of the enzyme or protein matrix and spacer may be driven by a variety of factors including, without limitation, the need to measure a physiological parameter, such as, for example, blood glucose.

The outer diameter of the first spacing element 50 may be greater than the inner diameter of the outer tubing 26. Thus, when the outer tubing 26 is expanded and chemically or mechanically fitted or otherwise formed over the first spacing element 50, the first spacing element 50 may be forced against the electrodes 36 on the substrate 30 by the contraction force of the outer tubing, thus forming a compression fit.

The height of the first spacing element 50 may extend beyond the height of the beads 22. When the height of the first spacing element 50 and the beads 22 are offset, any compression upon the first spacing element 50 tends to stabilize the dimensions of the elements of the apparatus. Thus, when the outer tubing is applied over the beads and spacing elements, the resulting compression of the first spacing element contributes to the dimensional stability of the recessed enzyme or protein matrix, for example. Thus, the durometer, or the hardness or softness, of the beads 22 and the first spacing element 50 may be modified to optimize the final shape or compression.

Figure 6:
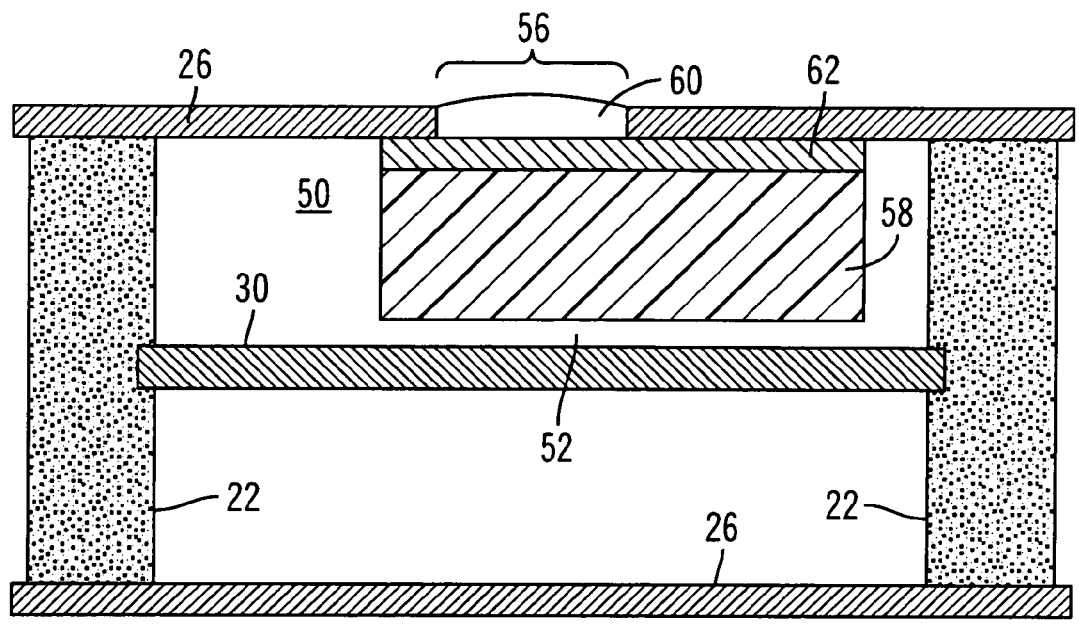
FIG. 6 is a cross-sectional side view showing a sensing window configuration in accordance with one or more embodiments of the invention.

FIG. 6 is a cut-away side view of the finished sensing apparatus in the vicinity of the window 56. As shown, the second spacing element 54 may be replaced with an enzyme or protein matrix 58. The enzyme or protein matrix may be any of a variety of enzymes, protein matrices, catalytic polymers, antibodies, combinations thereof and the like that may be employed for sensing. For example, if physiological parameter sensing is desired, one or more proteins may be used as the enzyme or protein matrix. According to one embodiment of the present invention, a combination of glucose oxidase and human serum albumin may be used concurrently in a solid matrix form to form a sensor matrix protein (SMP). The SMP may be cross-linked together or polymerized using gluteraldehyde or other suitable chemical such that a three-dimensional structure is created. According to another embodiment of the invention, the SMP may be immobilized in a silicone foam, such as, for example, any porous hydrophilic material or any non-hydrophilic material that is specially treated to encourage hydrophilicity. The SMP may reside in the "pores" of the foam and may be cross-linked in place. Also, the SMP may be immobilized in any other suitable matrix. According to yet another embodiment of the present invention, the SMP may be spun onto a surface of the spacer, or shim, or directly onto an electrode.

In the gap of window 56, above enzyme or protein matrix 58, a hydrogel layer 60 may be formed to seal the sensing apparatus and protect the enzyme or protein matrix 58 and other internal elements of the sensor from undesirable fluids, such as blood, or other fluids, that may exist in the implant environment. If the bond between the hydrogel layer 60 and the enzyme or protein matrix 58 is broken, and/or if the hydrogel layer 60 separates from the outer tubing 26 at the perimeter of the window 56, the hydrogel layer may become loose or even detached. Such a condition may result minimally in seepage of undesired fluids that may disrupt sensing performance, and may ultimately result in the digestion of the enzyme or protein matrix 58 and failure of the sensing device.

To enhance the strength of the bond between the enzyme or protein matrix 58 and the hydrogel layer 60, a bonding layer 62 may be applied between the enzyme or protein matrix 58 and the hydrogel layer 60. The bonding layer acts like a glue or sealant, providing additional bonds between the enzyme or protein matrix and the hydrogel for improved strength. The bonding layer also serves to improve the strength of the aperture itself, to resist expansion from enzyme or protein matrix swelling, for example. The bonding layer 62 may be made of any bio-compatible material that has adhesive properties, such as, for example, human serum albumin (HSA), though the material must still permit glucose (or other sensor-specific substance) to pass. Examples other than HSA may include, but are not limited to collagen, fibrin, or suitable synthetic materials (e.g., polypeptides), or any other adhesive.

The risk of compromising the integrity of the sensor may be reduced by minimizing the size of the sensor window, and, thus, the amount of fragile material, that is exposed. A minimized window provides less surface area to be damaged and a smaller perimeter around which leaks may form.

A smaller window may be formed in conjunction with a smaller sensor electrode (specifically, the "working" electrode aligned underneath the enzyme or protein matrix 58). The electrode, however, must be of sufficient length to provide sensing capability. For example, according to an embodiment of the present invention, an electrode must be of sufficient length to provide a 20 nA current at 2.5% oxygen. The decrease in electrode size may be facilitated by controlling the formation process associated with the electrode, such as, but not limited to deposition, etching, sputtering and the like. The electrode formation process may include, but is not limited to controlling an ion beam assisted deposition (IBAD) process used to form caps over electrode/via interfaces in the substrate 30. (The electrode/via interfaces are prone to attack by hydroxyl ions formed near the electrode. Thus, caps formed of hydroxyl ion inhibiting material, such as Alumina, sapphire, $Al_2O_3$ and the like may be utilized to protect those interfaces.) By increasing the IBAD caps, the effective electrode size may be decreased.

Figure 7:
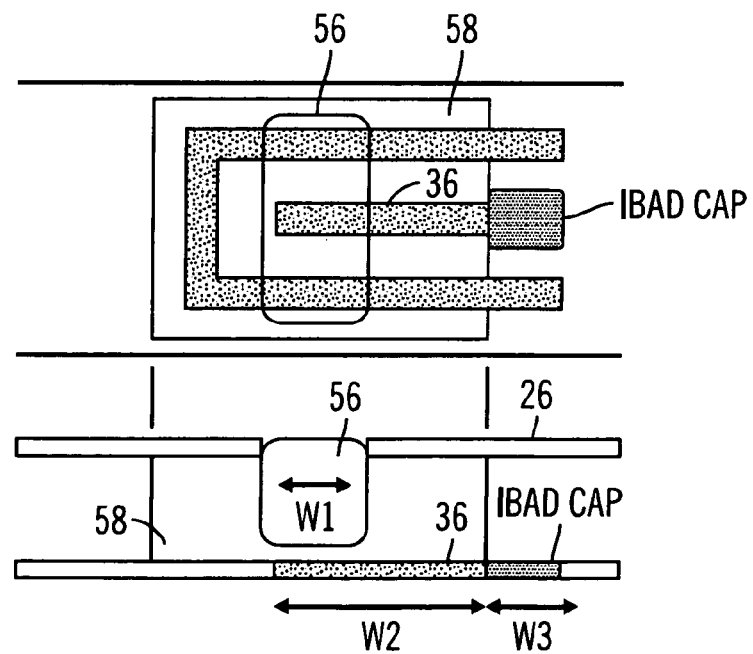
FIG. 7 is a top-down and side view of a sensing apparatus showing the position of a sensing window with respect to a sensing electrode in accordance with one or more embodiments of the invention.

FIG. 7 shows a side and top view of the relative sizes and positioning of the window 56 and the electrode 36.

Figure 8A:
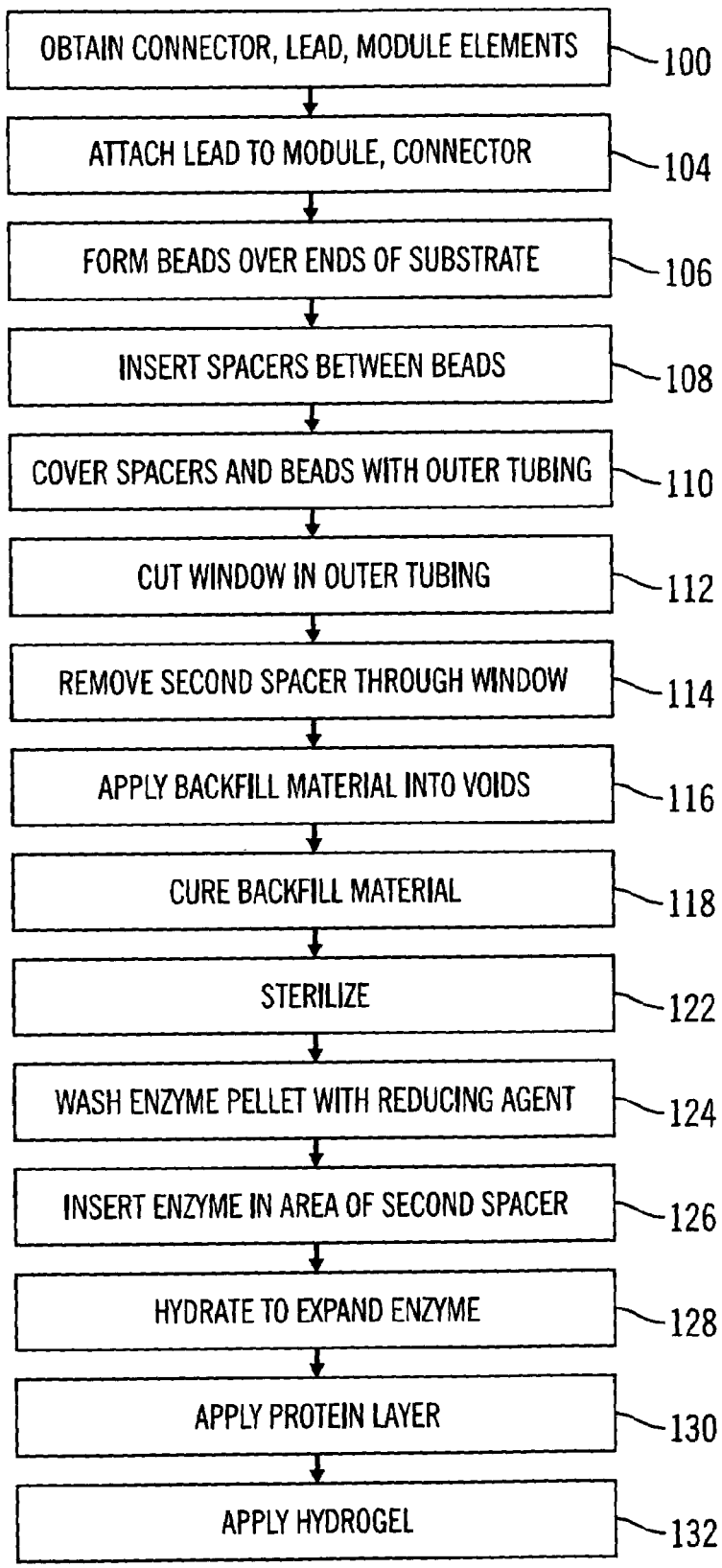
FIG. 8A is a flow diagram of a process for making a sensing apparatus in accordance with one or more embodiments of the invention.
Figure 8B:
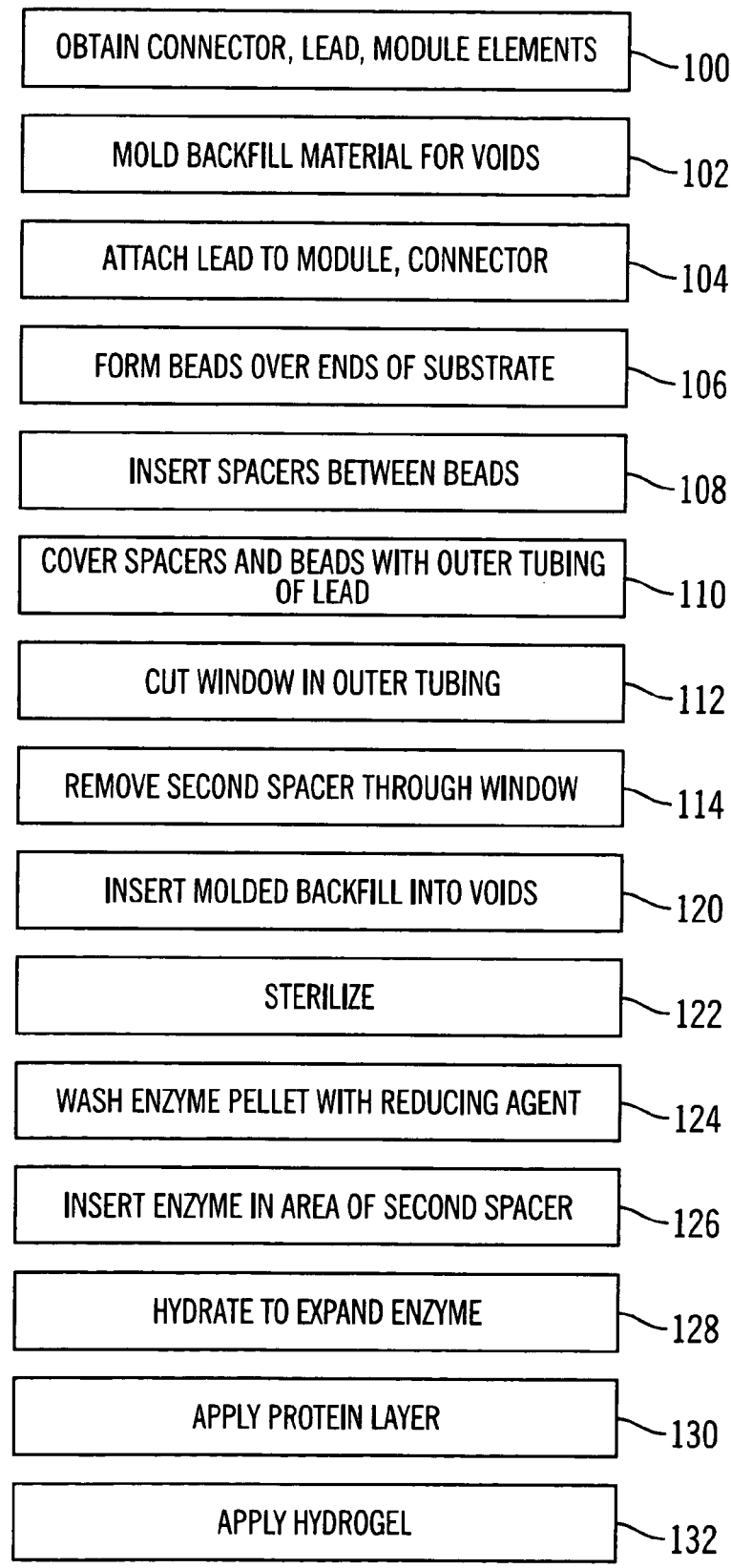
FIG. 8B is a flow diagram of a process for making a sensing apparatus, utilizing molded backfill elements, in accordance with one or more embodiments of the invention.

FIGS. 8A and 8B show processes for making a sensing apparatus according to embodiments of the present invention. Though shown as a sequence of steps for clarity, other implementations may alter the order of the steps presented, perform certain steps in parallel with others, and/or combine or omit certain steps without departing from the scope of the invention.

In FIG. 8A, at step 100, the connector 16, the sensor lead 12 and the elements of sensor module 20 (e.g., substrate 30, beads 22, spacing elements 50 and 54, and enzyme or protein matrix 58) are obtained. At step 104 the wires in the conductive element of the sensor lead 12 are attached to circuit pads on the substrate 30 of the sensor module 20 and to the connector 16. The wires in the conductive element may be welded, soldered, or otherwise attached to the pads and crimped, welded, soldered, or otherwise attached to the connector.

At step 106, beads 22 are formed over the ends of the substrate 30 such that the welding pads and the core 60 are encapsulated within the beads 22. In addition, an ogive tip 24 may be glued or otherwise attached to a bead 22 opposite the sensor lead 12.

At step 108, spacing elements may be inserted in between the beads 22. The spacers may comprise a first spacing element 50 and a second spacing element 54. At step 110, an outer tubing 26 of the sensor lead 12 may be pulled over the sensor module 20 and partially over the ogive tip 24 that is attached to the bead 22 opposite the sensor lead 12.

At step 112, a window may be formed in the outer tubing of the sensor lead 12 over the second spacing element 54. Formation of the window may include, but is not limited to, cutting, molding, or the like. The window may be placed in a manner suitable for the application of the sensing apparatus 10 and such that the sensitivity of the apparatus is advantageous. For example, if the sensing apparatus is to be used in a glucose monitoring application, such as might be used in the case of a diabetic, the window may be formed with a particular width and at such a place on the outer tubing of the sensor lead 12 such that oxygen (or other sensor specific chemical element or compound) influx into the enzyme or protein matrix is aided. In glucose sensing applications, a typical window width may be, but is not limited to, about five thousandths of an inch to about fifty thousands or seventy thousandths of an inch. In addition, window depth may be, but is not limited to, anywhere from about four thousandths of an inch to fifty thousandths of an inch. However, the dimensions of the window depend on the size of the device. The response time of the device may also be adjusted by the cut and placement of the window. Once the window opening has been formed, the second spacing element 54 may be removed at step 114.

The sensor device contains multiple elements, between which voids may exist, due, for example, to geometrical manufacturing tolerances. FIG. 9A provides a cross-sectional side view of the sensor device showing spatial void 80 in the sensor module. FIGS. 9B, 9C and 9D respectively provide an axial cross-sectional views at locations B, C and D along the sensor module in FIG. 9A. Spatial void (or voids) 80 may exist between the outer tubing 26 and internal elements of the sensor module. For example, voids 80 may exist between the outer tubing and the external edges of substrate 30 (as shown in FIGS. 9C, 9D), between the outer tubing 26 and the outer curved perimeter surface of first spacing element 50 (as shown in FIG. 9C), and between the outer tubing 26 and beads 22 (as shown in FIGS. 9B–9D).

Blood or other undesired fluids that diffuse into spatial void 80 create performance problems, such as causing short circuits in the electrical components and deterioration of the enzyme or protein matrix. To minimize these problems, the voids may be back-filled with a curable, implantable material at step 116 in FIG. 8A. Methods for applying the back-fill material include, but are not limited to, an injection process, a pre-molding and assembly process, or the like. The back-fill material may comprise, for example, but is not limited to, silicone, epoxy, bone cement, foam, gel or the like.

Back-filling may be accomplished, for example, by needle injection through the sensor window prior to placement of the enzyme or protein matrix pellet and window hydrogel. The back-fill material is obtained in a flowable state (e.g., liquid, gel, or other fluidic form) to facilitate use of a syringe. The tip of the syringe may then be used to apply the back-fill material into any existing spatial voids. Applicators other than a syringe may also be used, including, but not limited to a pipette. At step 118, after assurance of a proper fill, the fill material may be cured to a hardened or partially hardened, non-flowable state, such that the back-fill material remains in place. Mechanisms for curing the back-fill material include, but are not limited to exposure to heat, light, other radiation, a hardening catalyst, a chemical curing agent or other mechanisms typical in the art depending on the back-fill material used.

FIG. 8B shows an alternative embodiment wherein filling spatial voids 80 is accomplished with one or more pre-molded structures. Rather than implementing steps 116 and 118, FIG. 8B provides a step 102 (between steps 100 and 104) in which one or more appropriately configured pieces of fill material are molded prior to final assembly. Then, at step 120 (after step 114), the pre-molded back-fill pieces are inserted into the sensor to fill the voids. Step 120 may also be implemented between steps 108 and 110, i.e., just prior to the step of pulling the outer tubing 26 around the spacing elements.

Referring back to FIG. 8A, the entire sensing apparatus 10 may be sterilized at step 122, using any one or a combination of suitable sterilization techniques. For example, the entire sensing apparatus 10 (which may or may not include an enzyme, protein, or other physiological parameter sensor) may be put into an ethylene oxide (ETO) gas such that the ETO gas permeates all of the elements of the sensing apparatus 10. After sterilization, the sensing apparatus may be stored until it is ready for use. A sterilization method of this type is disclosed in U.S. patent application Ser. No. 10/034,505, filed Dec. 28, 2001, entitled "Sterile Device and Method of Producing Same," the contents of which are hereby incorporated herein by reference.

If desired, when the sensing apparatus is ready for use, an enzyme or protein matrix 58, in the form of an enzyme or protein matrix pellet, may be put in place of the second spacing element 54 through the window at step 126. According to an embodiment of the present invention, the enzyme or protein matrix may be hydrated at step 128 such that it expands to form a tight fit and to fill the area left by the removal of the second spacing element 54. According to an embodiment of the present invention, the enzyme or protein matrix may initially be in a slightly desiccated state when placed into the area vacated by the second spacing element 54. Although such a desiccated state facilitates placement, space may exist between the enzyme or protein matrix and the surround area of the sensor module 20. Thus, the surrounding area and the enzyme or protein matrix may be hydrated with a sterile buffer, thereby swelling the enzyme or protein matrix and forming a compression fit in the recess or receptacle of the first spacing element 50.

Apart from the desired enzyme or protein matrix expansion in step 128, the enzyme or protein matrix pellet may be prone to excessive swelling over time, particularly in the presence of peroxide. This excessive swelling behavior may have several undesirable consequences. For example, excessive swelling may destabilize the enzyme or protein matrix, rendering the enzyme or protein matrix more susceptible to attack. Further, enzyme or protein matrix swelling may expand the window aperture of the sensor, creating gaps around the window and possibly dislodging the outer hydrogel layer. Finally, the infusion path length may increase as the enzyme or protein matrix volume increases, reducing the sensitivity of the sensor.

In accordance with one or more embodiments, excessive enzyme or protein matrix swelling may be alleviated by washing the enzyme or protein matrix pellet with a reducing agent in step 124 (i.e., just prior to enzyme or protein matrix insertion in step 126). Any reducing agent that will not harm the enzyme or protein matrix, such as sodium cyanoborohydride, may be used. However, Ascorbate may be preferred for its milder properties. The reducing agent reduces the Schiff base bond within the enzyme or protein matrix, which allows for bond stabilization through cross-linking.

Figure 10A:
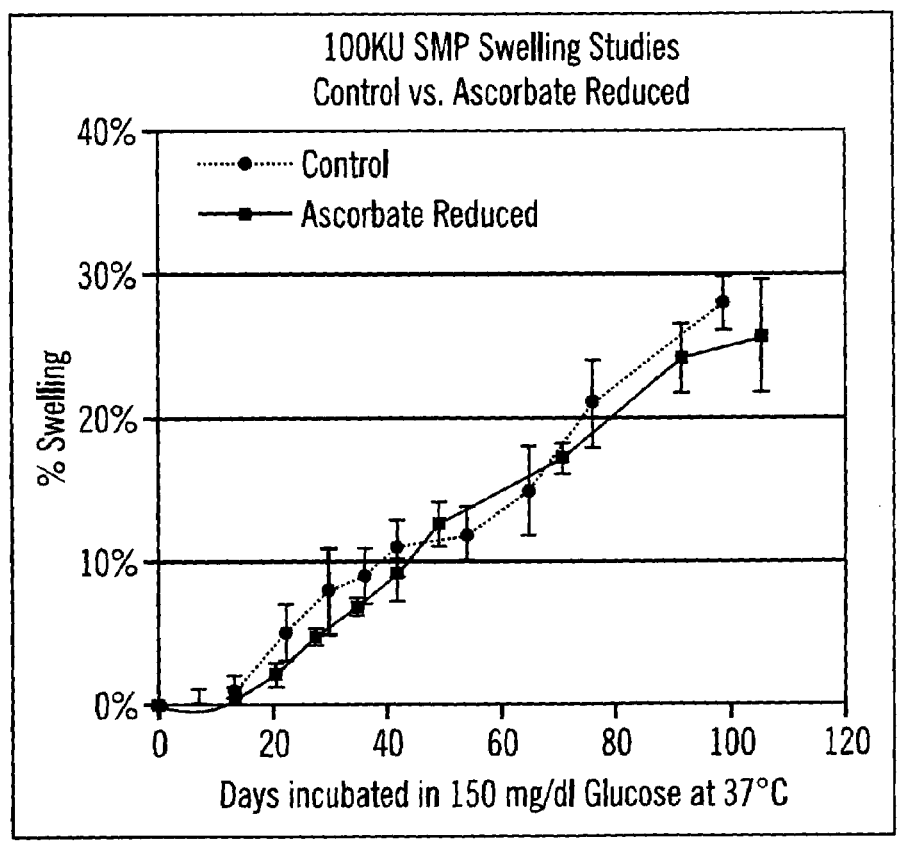
FIG. 10A is a graph illustrating test results showing the percentage swelling versus time in a glucose environment for an untreated enzyme or protein matrix and for an enzyme or protein matrix washed with a reducing agent.
Figure 10B:
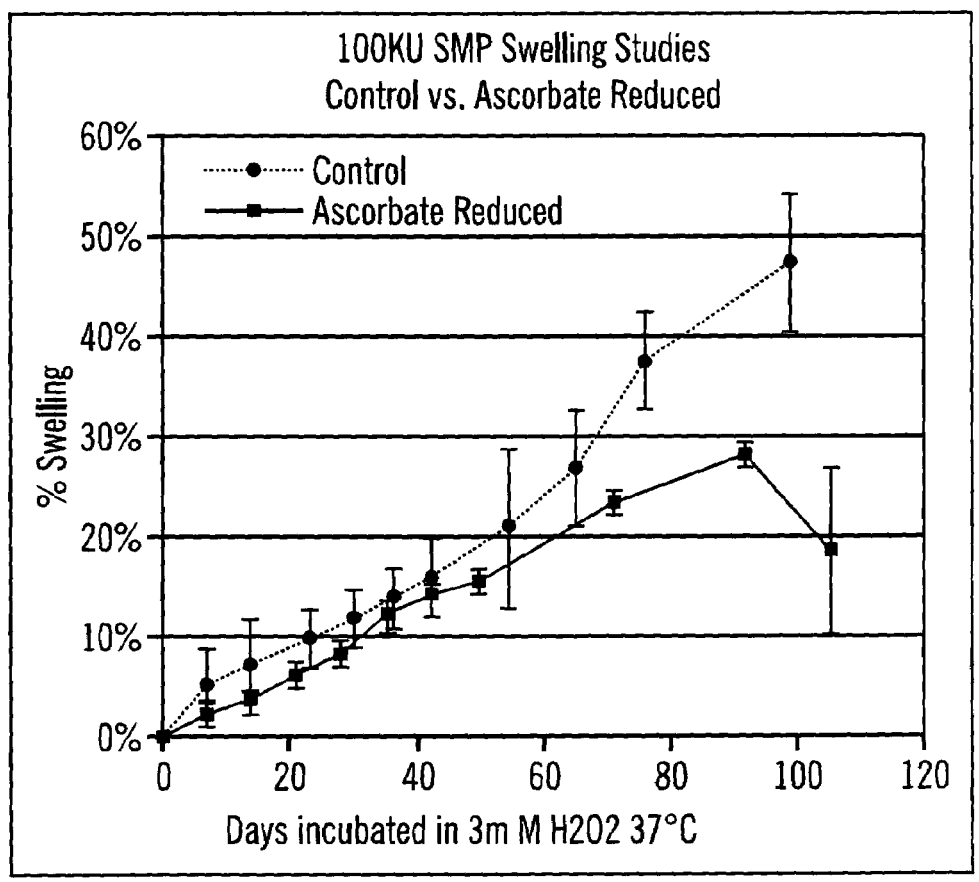
FIG. 10B is a graph illustrating test results showing the percentage swelling versus time in a peroxide environment for an untreated enzyme or protein matrix and for an enzyme or protein matrix washed with a reducing agent.

To illustrate the decrease in swelling achieved through enzyme or protein matrix treatment with a reducing agent, FIGS. 10A and 10B show approximate test results obtained regarding the percentage of enzyme or protein matrix swelling observed versus time of exposure of the enzyme or protein matrix to glucose and peroxide, respectively. Each graph plots the swelling behavior for an untreated (i.e., control) enzyme or protein matrix and an enzyme or protein matrix treated with Ascorbate. It can be seen, particularly in the peroxide environment, that the Ascorbate reduced enzyme or protein matrix experiences far less swelling over time than the control enzyme or protein matrix, particularly over the long term. Thus, the enzyme or protein matrix treated with the reducing agent is less likely to create problems with the integrity of the sensor.

An example embodiment of an enzyme or protein matrix treatment process includes washing the enzyme or protein matrix pellet in a solution with a 30 mM concentration of Ascorbate for two hours at room temperature, under constant agitation. The duration may be shortened under a higher temperature, though too high a temperature may deactivate the enzyme or protein matrix. Different concentrations of the reducing agent may be appropriate for different reducing agents and/or different enzymes or protein matrices.

Referring back to FIG. 8A, after the enzyme or protein matrix has been inserted and/or hydrated (i.e., steps 126 and 128), a bonding layer 62, having the adhesive properties of a protein, may be applied over the enzyme or protein matrix at step 130. The bonding layer 62 may be applied, for example, in liquid form, with a volumetric dispenser, such as a syringe or dropper. Other application methods may include, but are not limited to swabbing or using a pipette. Once applied, the liquid bonding layer 62 may be fixed with a cross-linking agent, such as, for example, gluteraldehyde.

The bonding layer 62 may be made of any bio-compatible material that has the adhesive properties of a protein, such as human serum albumin (HSA), though the material must still permit glucose (or other sensor-specific substance) to pass. Examples other than HSA may include, but are not limited to collagen, fibrin, or suitable synthetic materials (e.g., polypeptides).

At step 132, the remaining window cavity is sealed by application of, for example, a hydrogel, such as methacrylate, other hydrophilic acrylic, or the like, that is permeable to the analyte. The hydrogel layer 60 may be applied directly over the protein layer 62. Subsequently, the hydrogel may be polymerized using a UV polymerization process. In the case of a glucose sensor, the hydrogel may be permeable to glucose. Similarly, for other types of sensors, the hydrogel may be selectively permeable to the specified sensor target chemical.

Figure 11:
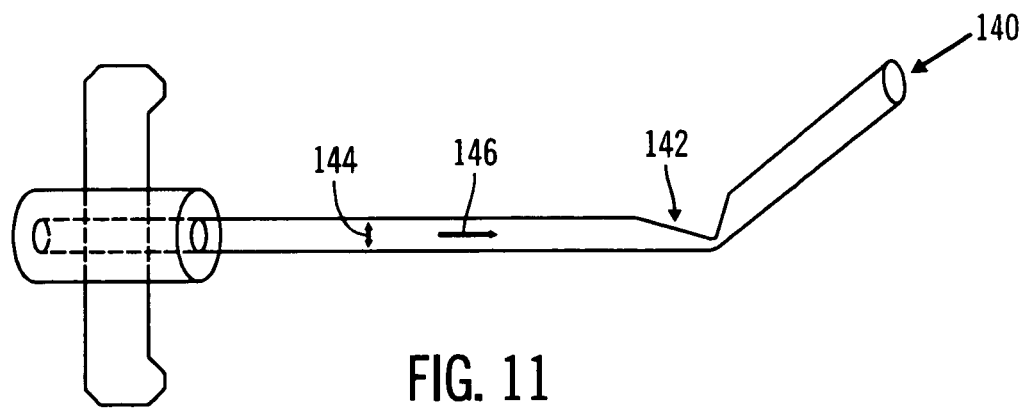
FIG. 11 is perspective view of an introducer having a kink.
Figure 13:
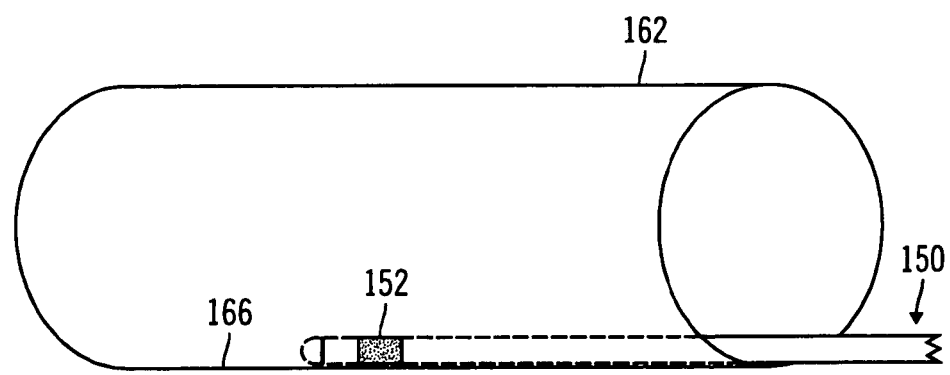
FIG. 13 is a perspective view of an insufficiently stiff sensor lead inserted into a vessel.

Referring back to FIG. 11, an insufficiently stiff or lubricious sensor may buckle under axial pressure when diverted through the introducer 140. Referring back to FIG. 13, the position of the sensor 152 in the vessel 162 is not optimal. According to embodiments of the present invention, in order to reduce the likelihood of damage to the sensor structure during implantation and to provide better positioning of the sensor lead within the vessel, a siloxane coating may be deposited on the outer diameter surface of a silicone tubing used for the leads of the sensor. The siloxane coating provides stiffening and lubrication to the silicone tubing. The added lubricity reduces surface friction during implantation of the sensor. The added stiffness improves the steerability through the introducer, allowing the sensor lead to more easily bypass any kinks in the introducer.

According to embodiments of the present invention, the siloxane may be applied as a coating on the silicone tubing through plasma induced deposition. An example of the plasma induced deposition process is described in U.S. Pat. No. 6,263,249, entitled "Medical electrical lead having controlled texture surface and method of making same." According to one embodiment, a hexamethylsilane vapor reacts to form a hexamethyldisiloxane coating on the surface of the silicone. According to other embodiments of the present invention, the siloxane coating may be applied by other methods, including, but not limited to, dipping or spraying the silicone tubing.

According to another embodiment of the present invention, in order to reduce the likelihood of damage to the sensor structure during implantation and to provide better positioning of the sensor lead within the vessel, an inner silicone tube of the sensor lead may be replaced with a tube made from an elastomeric material having a sufficient durometer value to provide suitable stiffness to the sensor lead to avoid buckling or damage to the sensor lead during advancement of the sensor lead through the introducer. In one embodiment, a sufficient durometer value of the elastomeric material is approximately 55. The elastomeric material used may be a polyurethane material, a hybrid silicone-polyurethane material, or other suitable elastomeric material having a sufficient durometer value. The added stiffness provided by the inner tube formed from the elastomeric material increases steerability through the introducer and into the desired vessel. Thus, the sensor lead may be more easily advanced and implanted in the desired vessel, without employing a stylet or other tool that may damage the sensor.

According to another embodiment of the present invention, the sensor could be stiffened with a permanent wire inside the lead. The wire could be made from a variety of materials, such as, for example, stainless steel, nitinol and the like.

Embodiments of the present invention adding a lubricious coating and replacing an inner silicone tube with a tube made from an elastomeric material provide added stiffness to the sensor lead. In addition, the plasma induced siloxane deposition embodiment adds lubricity to the sensor lead. These embodiments of the present invention may be used separately or in combination.

Figure 14:
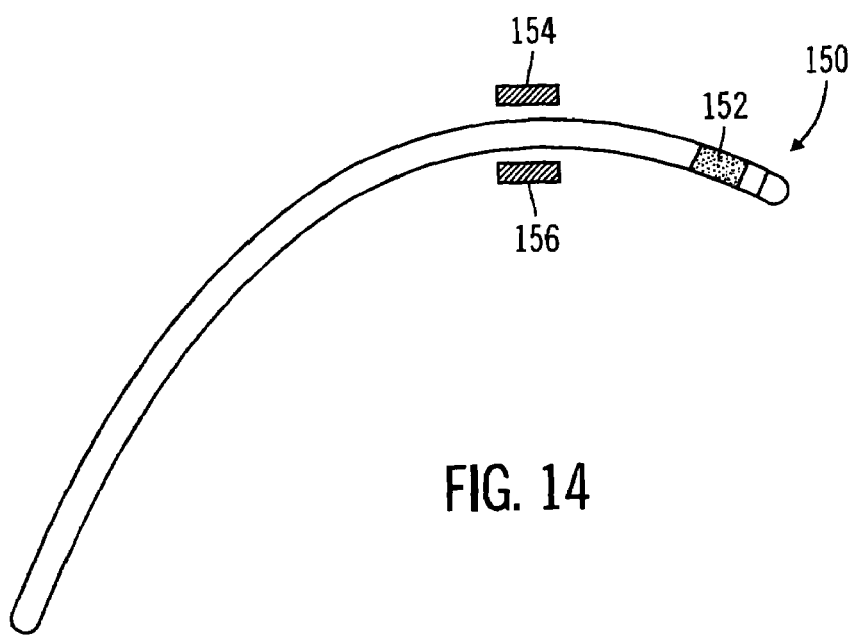
FIG. 14 is a side view detailing a gripping point of a sensor lead located distal from the sensor according to an embodiment of the present invention.

As shown in FIG. 14, due to the added stiffness and lubricity of the sensor lead provided by embodiments of the invention, the sensor lead 150 may advantageously be placed in the introducer 140 (shown in FIG. 11) by gripping the sensor lead 150 at a point sufficiently distant from the sensor 152 so that the sensor 152 will not be damaged. In addition, the stiffer sensor lead is more easily steered through the introducer. In portions of the introducer where kinks exist, the added stiffness and lubricity of the sensor lead allows the axial force of the sensor lead to translate through the sensor and straighten the kinks in the introducer.

Figure 15:
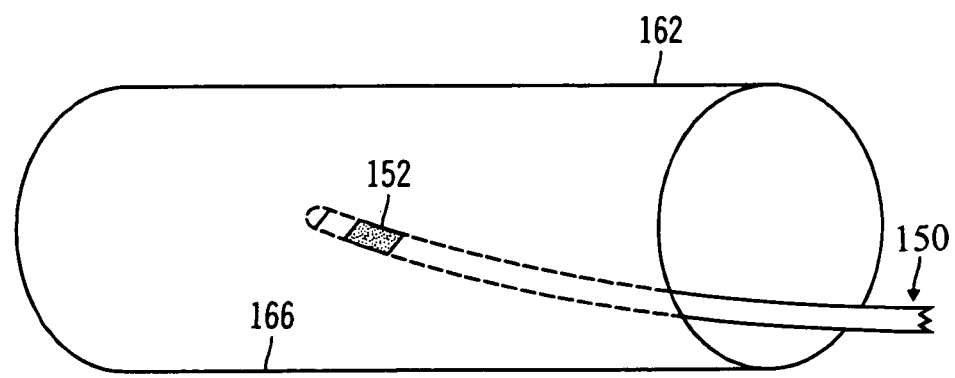
FIG. 15 is a perspective view a sufficiently stiff sensor lead inserted into a vessel according to an embodiment of the present invention.
Figure 12A:
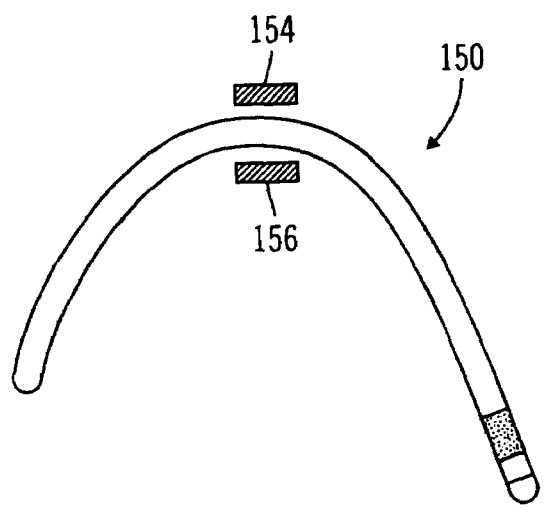
FIG. 12A is a side view detailing a gripping point of a sensor lead located distal from the sensor.
Figure 12B:
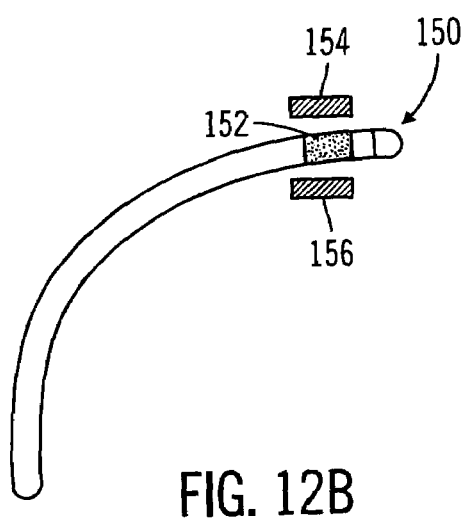
FIG. 12B is a side view detailing a gripping point of a sensor lead located proximal to the sensor.

In addition, as shown in FIG. 15, due to the added stiffness of the sensor lead 150 provided by embodiments of the invention, the sensor lead 150 is advantageously positioned away from the side-wall 166 of the vessel 162 despite gravitational forces that may be acting on the sensor lead 150 to push the sensor lead 150 to the side-wall 166, such as, for example, a prone or supine position of a person into which the sensor lead 150 has been inserted. The stiffer sensor may be lifted into the flow, i.e., a more centralized position within the vessel 162, due to lift and/or drag forces. In contrast, for prior art sensor leads, gravity may have a greater influence on the position of the sensor lead in the vessel. This positioning of the sensor 152 may result in more accurate sensor readings.

Thus, an implantable sensor device and a method of making such a sensor device have been described in conjunction with one or more embodiments. Various embodiments share the advantages earlier described, such as enhanced window integrity. Though especially advantageous when used in conjunction with the earlier described sensor embodiments, it will be understood by one skilled in the art that the sensor structure and manner of making are not limited to such sensor embodiments. The foregoing description of embodiments of the invention has been presented for the purposes of illustration and description. It is not intended to be exhaustive or to limit the invention to the precise form disclosed. Many modifications and variations may be possible in light of the above teaching. The invention is defined by the following claims and their full scope of equivalents.

What is claimed is:

1. An implantable sensing apparatus comprising:
   a substrate having an electrode;
   an outer tubing surrounding said substrate, said outer tubing having a window opening; and an enzyme aligned between said electrode and said window opening, said enzyme treated with a reducing agent to inhibit excessive swelling.

2. The apparatus of claim 1, wherein said reducing agent comprises Ascorbate.

3. The apparatus of claim 1, wherein said reducing agent comprises cyanoborohydride.

4. The apparatus of claim 1, wherein the outer tubing is coated with a lubricious coating.

5. The apparatus of claim 4, wherein the lubricious coating is siloxane.

6. The apparatus of claim 1, further comprising an inner tubing disposed within an interior of the outer tubing.

7. The apparatus of claim 6, wherein the inner tubing is made from an elastomeric material.

8. The apparatus of claim 6, wherein the inner tubing is made from a metal.

9. An implantable sensing apparatus comprising:
   a substrate comprising an electrode;
   an outer tubing surrounding said substrate, said outer tubing having a window opening;
   an enzyme aligned between said electrode and said window opening;
   a hydrogel layer sealing said window opening; and
   a bonding layer between said enzyme and said hydrogel layer, said bonding layer being a different material from said enzyme;
   wherein the bonding layer comprises a protein, human serum albumin (HSA), or a polypeptide.

10. The apparatus of claim 9, wherein said bonding layer comprises a protein.

11. The apparatus of claim 9, wherein said bonding layer comprises human serum albumin (HSA).

12. The apparatus of claim 9, wherein said bonding layer comprises a polypeptide.

13. The apparatus of claim 9, wherein said bonding layer comprises an adhesive.

14. The apparatus of claim 9, wherein the outer tubing is coated with a lubricious coating.

15. The apparatus of claim 14, wherein the lubricious coating is siloxane.

16. The apparatus of claim 9, further comprising an inner tubing disposed within an interior of the outer tubing.

17. The apparatus of claim 16, wherein the inner tubing is made from an elastomeric material.

18. The apparatus of claim 16, wherein the inner tubing is made from a metal.

19. The apparatus of claim 9, wherein the enzyme comprises a protein matrix.

20. The apparatus of claim 9, wherein said bonding layer is free of said enzyme.

21. The apparatus of claim 9, wherein said bonding layer is chemically free of said enzyme.

22. The apparatus of claim 9, wherein said bonding layer is only on one side of said enzyme.

23. The apparatus of claim 9, wherein said bonding layer prevents said enzyme from directly contacting said hydrogel layer.

24. An implantable sensing apparatus comprising:
   a substrate comprising an electrode;
   a spacing element adjacent to said substrate;
   an outer tubing surrounding said substrate and said spacing element, said outer tubing having a window opening, wherein geometrical tolerances between said outer tubing and one or more of said spacing element and said substrate define one or more voids;
   a backfill structure filling said one or more voids, said backfill structure comprising a curable, implantable material;
   an enzyme aligned between said electrode and said window opening, said enzyme being pre-treated with a reducing agent;
   a layer of hydrogel sealing said window above said enzyme; and
   a layer of protein bonding said enzyme to said layer of hydrogel.

25. The apparatus of claim 24, wherein the outer tubing is coated with a lubricious coating.

26. The apparatus of claim 25, wherein the lubricious coating is siloxane.

27. The apparatus of claim 24, further comprising an inner tubing disposed within an interior of the outer tubing.

28. The apparatus of claim 27, wherein the inner tubing is made from an elastomeric material.

29. The apparatus of claim 27, wherein the inner tubing is made from a metal.

30. The apparatus of claim 24, wherein the enzyme comprises a protein matrix.

* * * * *